(12) United States Patent
Comte et al.

(10) Patent No.: US 7,357,918 B2
(45) Date of Patent: Apr. 15, 2008

(54) MICROPIGMENT MIXTURES

(75) Inventors: Christine Comte, Huningue (FR); Sébastien Mongiat, Sierentz (FR)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 443 days.

(21) Appl. No.: 10/503,151

(22) PCT Filed: Jan. 23, 2003

(86) PCT No.: PCT/EP03/00619

§ 371 (c)(1),
(2), (4) Date: Jul. 28, 2004

(87) PCT Pub. No.: WO03/063814

PCT Pub. Date: Aug. 7, 2003

(65) Prior Publication Data

US 2005/0196360 A1    Sep. 8, 2005

(30) Foreign Application Priority Data

Jan. 31, 2002 (EP) .................................. 02405061

(51) Int. Cl.
  *A61Q 17/04* (2006.01)
  *A61Q 17/00* (2006.01)
  *A61Q 19/04* (2006.01)
  *A61Q 19/00* (2006.01)
  *A61K 8/02* (2006.01)

(52) U.S. Cl. .................... 424/59; 424/60; 424/400; 424/401

(58) Field of Classification Search .................. 424/59, 424/60, 400, 401
  See application file for complete search history.

(56) References Cited

U.S. PATENT DOCUMENTS 6,416,748 B1 * 7/2002 Candau et al. ................. 424/59

2001/0028886 A1 * 10/2001 Robert et al. ................ 424/401
2002/0155073 A1   10/2002 Fankhauser et al. .......... 424/59

FOREIGN PATENT DOCUMENTS

EP    1068866    1/2001
EP    1093798    4/2001

OTHER PUBLICATIONS

Li Guo-hui et al., Chemistry World, "Surface Modification of Nanosized Titanium Dioxide Particles as Ultraviolet Absorbent in Cosmetics", 2000(2), pp. 59-63.
Chem. Abstract 137:24104 of Research Disclosure 449030 (2001).

* cited by examiner

Primary Examiner—Shelley A. Dodson
(74) Attorney, Agent, or Firm—Mervin G. Wood

(57) ABSTRACT

Disclosed is a UV absorber mixture, comprising (a) 1% to 60% of a micronised UV broadband absorber of formula: Formula (I); wherein $R_1$ is $C_1$-$C_{12}$alkyl; or phenyl-substituted $C_1$-$C_{12}$alkyl; and (b) 1% to 60% by weight of a water dispersible and/ir oil-dispersible coated titanium di-oxide. The UV absorber mixture shows synergistic effect with respect to the UPF

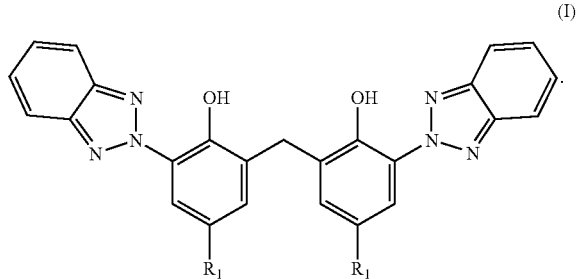

(I)

8 Claims, No Drawings

MICROPIGMENT MIXTURES

The present invention relates to the use of mixtures of micronised inorganic and organic UV filters in protecting human and animal skin and hair against the damaging effect of UV radiation and to their use in cosmetic and pharmaceutical formulations.

It is known that certain organic UV filters, for example sparingly soluble benzotriazole or triazine compounds, exhibit pronounced UV filtering properties when they are in the form of single compounds in micronised form. By virtue of their specific, substance-typical properties, however, they only ever absorb, reflect or scatter a certain portion of the damaging UV range.

Certain inorganic substances have also been proposed for the use as sunscreens, which physically block exposures to the skin to UV rays. Notable of these is titanium dioxide having a very small particle size. This grade of titanium dioxide, designated ultra fine $TiO_2$, affords a good degree of sun blocking potential without the unacceptable skin whitening effect.

Surprisingly it was found that mixtures of specific micronised organic UV absorbers and micronised inorganic pigments show synergistic effect with respect to their SPF values. In addition, a ternary synergy is noticed when the above-mentioned UV absorber mixture is combined with one the UV absorber mentioned in Table 1.

Therefore, the present invention relates to a UV absorber mixture comprising (a) 1 to 60, preferably 20 to 40% by weight of a micronised UV broadband absorber of formula

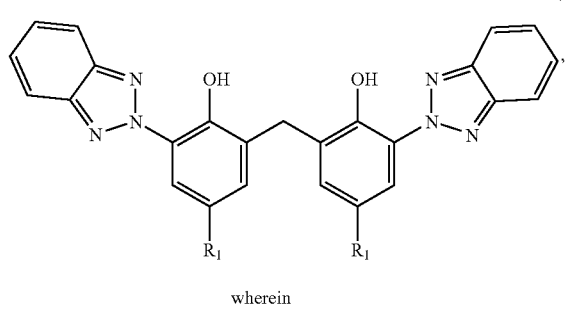

(1)

wherein $R_1$ is $C_1$-$C_{12}$alkyl, preferably tert-butyl, or phenyl-substituted $C_1$-$C_{12}$alkyl; and (b) 1% to 60, preferably 10 to 60, and most preferably from 20 to 40% by weight of a water dispersible and/or oil-dispersible coated titanium dioxide.

$R_1$ in formula (1) is preferably methyl, tert-butyl or, most preferably, iso-octyl.

By "micronised $TiO_2$" is meant particles of titanium dioxide having an average primary particle size of less than 200 nm, preferably from 10 to 100 nm and most preferably from 25 to 60 nm.

In order to reduce the photo-oxidative drawbacks of these micro-fine metal oxides when co-irradiated with organic compounds, a pre-coating with inorganic compounds such as silica ($SiO_2$), alumina ($Al_2O_3$), aluminum hydroxide ($AlOH_3$) or zirconium dioxide ($ZrO_2$) of a percentage range between 2% to 15% is needed.

Furthermore, organic treatments (surface coating) are frequently used to improve the dispersibility of the microfine particles of $TiO_2$; Examples for organic substances are fatty acids and its derivatives (metal soaps) or silicones like methicone, dimethicone or triethoxy caprylyl silane, or the substances disclosed in European UV Sun Filters Conference Proceedings, Benefits of surface coating on micro-fine oxides, T. Miyoshi and al., Miyoshi Kasei Inc., Chapter "Surface-coated micro-fine metal oxides", pp 84-85.

Water-dispersible titanium dioxide is micronised titanium dioxide, the particles of which are coated with a material to impart a hydrophilic surface property to particles. Examples of such materials include silica, iron oxide alumina or zinc.

Oil-dispersible titanium dioxide, in accordance with the present invention, is micronised titanium dioxide, the particles of which exhibit a hydrophobic surface property, and, which for this purpose, are coated with metal soaps like polymethylmethycrylate, isopropyl titanium triisostearate, aluminium stearate, magnesium stearate, aluminium laurate or zinc stearate, methyl hydrogen polysiloxane, oxygenated polysiloxane, glycerine, stearyl alcohol, Steareth-7, Steareth-10, stearic acid, lauric acid, simethicone or dimethicone.

The micronised titanium dioxide can be incorporated either in the water phase (water-dispersible) or in the oil phase (oil-dispersible) during the manufacturing of the cosmetic end-formulations.

In a further embodiment of the present invention mixtures of both water-dispersible micronised titanium dioxide and oil-dispersible titanium dioxide are used in the present UV absorber mixture.

The UV absorber mixture suitable for use according to the invention can be prepared in various ways:

In a first method, the benzotriazole UV absorber of formula (1) (component (a)) and the titanium dioxide (component (b)) can be mixed, as single substances, during the process for the preparation, i.e. the micronisation of the microparticles (=comicronisation).

A further possible preparation method comprises intimately mixing together the single substances of the UV filters, which have been micronised before.

A third possible preparation method comprises melting together at least two of the UV filters mentioned above. After the melt has cooled, a homogeneous composite is obtained, which is micronised in customary manner.

Any known process suitable for the preparation of microparticles can be used for the preparation of the micronised UV absorbers, for example:

wet-milling (low viscous micronisation process for pumpable dispersions), with a hard grinding medium, for example zirconium silicate balls in a ball mill and a protective surfactant or a protective polymer in water or in a suitable organic solvent;

wet-kneading (high viscous micronisation process non pump-able pastes) using a continuous or discontinuous (batch) kneader. For a wet-kneading process a solvent (water or cosmetically acceptable oils), a grinding-aid (surfactant, emulsifier) and a polymeric grinding aid may be used.

Both processes may be used respectively spray-drying from a suitable solvent, for example aqueous suspensions or suspensions containing organic solvents, or true solutions in water, ethanol, dichloroethane, toluene or N-methylpyrrolidone etc.

by the expansion according to the RESS process (Rapid Expansion of Supercritical Solutions) of supercritical fluids (e.g. $CO_2$) in which the UV filter or filters is/are dissolved, or the expansion of fluid carbon dioxide together with a solution of one or more UV filters in a suitable organic solvent;

by reprecipitation from suitable solvents, including supercritical fluids (GASR process=Gas Anti-Solvent Recrystallisation/PCA process=Precipitation with Compressed Anti-solvents).

As milling apparatus for the preparation of the micronised organic UV absorbers there may be used, for example, a jet mill, ball mill, vibratory mill or hammer mill, preferably a high-speed mixing mill. Even more preferably mills are modern ball mills, manufactures of these mill-types are for example Netzsch (LMZ-mill), Drais (DCP-viscoflow or cosmo), Bühler AG (centrifugal mills) or Bachhofer. The grinding is preferably carried out with a grinding aid. As kneading apparatus for the preparation of the micronised organic UV absorbers examples are typical sigma-hook batch kneaders but also serial batch kneaders (IKA-Werke) or continuous kneaders (Contiuna from Werner und Pfleiderer).

Useful low molecular weight grinding aids for all the above micronizing processes are surfactants and emulsifies as disclosed below in the chapters "emulsifiers" and "surfactants".

Useful polymeric grinding aids for water dispersion are cosmetically acceptable water soluble Polymers with Mw>5000 g/mol for example: Acrylates (Salcare types), modified or non-modified polysaccharides, polyglucosides or xanthan gum. Furthermore an alkylated vinylpyrrolidone polymer, a vinylpyrrolidone/vinyl acetate copolymer, an acyl glutamate, an alkyl polyglucoside, ceteareth-25 or a phospholipid may be used. Oil dispersions may contain cosmetically acceptable waxy polymers or natural waxes as polymeric grinding aid to adjust viscosity during and after processing.

Useful solvents are water, brine, (poly-)ethylenglycol or glycerine for water-soluble dispersions and also cosmetically acceptable oils like described under "emollients" for oil-soluble dispersions.

The micronised UV absorbers so obtained usually have an average particle size from 0.02 to 2 micrometer, preferably from 0.05 to 1.5 micrometer and more especially from 0.1 to 1.0 micrometer.

The micronized UV absorber mixture can also be used dry in powder form. For that purpose the UV absorbers are subjected to known grinding methods, such as vacuum atomization, countercurrent spray-drying etc. Such powders have a particle size of from 0.1 micrometer to 2 micrometer. To avoid the occurrence of agglomeration, the UV absorbers can be coated with a surface-active compound prior to the pulverisation process, for example with an anionic, non-ionic or amphoteric surfactant, e.g. a phospholipid or a known polymer, such as PVP, an acrylate etc.

By virtue of their lipophilicity, they can satisfactorily be incorporated, alone or together with other soluble organic UV absorbers, into oil-containing and fat-containing cosmetic formulations, such as oils, O/W or W/O emulsions, fatty sticks or gels, in accordance with known methods.

The cosmetic formulations or pharmaceutical compositions according to the present invention can additonally contain one or more than one further UV filter as described in table 1-3.

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, for example octyl methoxy cinnamate, salicylic acid isooctyl ester, etc. The UV absorber can be used, for example, without further treatment, or in the micronised state, or in the form of a powder.

Cosmetic or pharmaceutical preparations contain from 0.05-40% by weight, based on the total weight of the composition, of the UV absorber mixture of the present invention or the UV absorber mixture of the present invention together with other UV-absorbers.

Preference is given to the use of mixing ratios of the present UV absorber mixture and optionally further light-protective agents (as described in table 1-3) from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably approximately 50:50. Such mixtures can be used, inter alia, to improve solubility or increase UV absorption.

The UV absorber mixture according to the present invention or combinations of UV filters are useful to protect skin, hair and/or natural or artificial hair color.

TABLE 1

Suitable UV filter substances which can be additionally used with the UV absorbers according to the present invention p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
dibenzoylmethane derivatives, for example 1-(4-tert-butylphenyl)-3-(4-methoxyphenyl)-propane-1,3-dione;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, US-A-5 338 539, US-A-5 518 713 and EP-A-613 893;
polymeric UV absorbers, for example the benzylidene malonate derivatives described in EP-A-709 080;
cinnamic acid derivatives, for example the 4-methoxycinnamic acid 2-ethylhexyl ester and isoamyl ester or cinnamic acid derivatives described in US-A-5 601 811 and WO 97/00851;
camphor derivatives, for example 3-(4'-methyl)benzylidene-bornan-2-one, 3-benzylidene-bornan-2-one, N-[(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid)and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-

TABLE 1-continued

Suitable UV filter substances which can be additionally used with the UV absorbers according to the present invention propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in US-A-5 332 568, EP-A-517 104, EP-A-507 691, WO 93/17002 and EP-A-570 838;
2-phenylbenzimidazole-5-sulfonic acid and salts thereof;
menthyl o-aminobenzoates;

TABLE 2

Suitable UV filter substances which can be additionally used with the UV absorbers according to the present invention are described in the following patents (Abbreviations T: table, R: row, Comp: compound, Ex: compound(s) of patent example, p: page)

| | |
|---|---|
| DE 100331804 | Tab 1 p 4, tab 2 + 3 p 5 |
| EP 613893 | Ex 1-5 + 15, T 1, pp 6-8 |
| EP 1000950 | Comp. in table 1, pp 18-21 |
| EP 1005855 | T 3, p 13 |
| EP 1008586 | Ex 1-3, pp 13-15 |
| EP 1008593 | Ex 1-8, pp 4-5 |
| EP 1027883 | Compound VII, p 3 |
| EP 1027883 | Comp I-VI, p 3 |
| EP 1028120 | Ex 1-5, pp 5-13 |
| EP 1059082 | Ex 1; T 1, pp 9-11 |
| EP 1060734 | T 1-3, pp 11-14 |
| EP 1064922 | Compounds 1-34, pp 6-14 |
| EP 1081140 | Ex 1-9, pp 11-16 |
| EP 1103549 | Compounds 1-76, pp 39-51 |
| EP 1108712 | 4,5-Dimorpholino-3-hydroxypyridazine |
| EP 1123934 | T 3, p 10 |
| EP 1129695 | Ex 1-7, pp 13-14 |
| EP 1167359 | Ex 1 p 11 and ex 2 p 12 |
| EP 420707 B1 | Ex 3, p 13 (CAS Regno 80142-49-0) |
| EP 503338 | T 1, pp 9-10 |

TABLE 2-continued

Suitable UV filter substances which can be additionally used with the UV absorbers according to the present invention are described in the following patents (Abbreviations T: table, R: row, Comp: compound, Ex: compound(s) of patent example, p: page)

| | |
|---|---|
| EP 517103 | Ex 3, 4, 9, 10 pp 6-7 |
| EP 517104 | Ex 1, T 1, pp 4-5; Ex 8, T 2, pp 6-8 |
| EP 626950 | all compounds |
| EP 669323 | Ex 1-3, p 5 |
| EP 780382 | Ex 1-11, pp 5-7 |
| EP 823418 | Ex 1-4, pp 7-8 |
| EP 826361 | T 1, pp 5-6 |
| EP 832641 | Ex 5 + 6 p 7; t 2, p 8 |
| EP 832642 | Ex 22, T 3 pp, 10-15; T 4, p 16 |
| EP 852137 | T 2, pp 41-46 |
| EP 858318 | T 1, p 6 |
| EP 863145 | Ex 1-11, pp 12-18 |
| EP 895776 | Comp. in rows 48-58, p 3; R 25 + 33, p 5 |
| EP 911020 | T 2, p 11-12 |
| EP 916335 | T 2-4, pp 19-41 |
| EP 924246 | T 2, p 9 |
| EP 933376 | Ex 1-15, pp 10-21 |
| EP 944624 | Ex 1 + 2, pp 13-15 |
| EP 945125 | T 3 a + b, pp 14-15 |
| EP 967200 | Ex 2; T 3-5, pp 17-20 |
| EP 969004 | Ex 5, T 1, pp 6-8 |
| JP 2000319629 | CAS Regno. 80142-49-0, 137215-83-9, 307947-82-6 |
| US 5635343 | all compounds on pp 5-10 |
| US 5338539 | Ex 1-9, pp 3 + 4 |
| US 5346691 | Ex 40, p 7; T 5, p 8 |
| US 5801244 | Ex 1-5, pp 6-7 |
| WO 0149686 | Ex 1-5, pp 16-21 |
| WO 0168047 | Tables on pp 85-96 |
| WO 0181297 | Ex 1-3 pp 9-11 |
| WO 0238537 | All compounds p 3, compounds on rows 1-10 p 4 |
| WO 9217461 | Ex 1-22, pp 10-20 |
| WO 9220690 | Polymeric comp in examples 3-6 |
| WO 9301164 | T 1 + 2, pp 13-22 |
| WO 9714680 | Ex 1-3, p 10 |

TABLE 3

Suitable UV filter substances which can be additionally used with the UV absorbers according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts | 56039-58-8 |
| 11 | 1-[4-(1,1-dimethylethyl)phenyl]-3-(4-methoxyphenyl)propane-1,3-dione | 70356-09-1 |
| 12 | Methyl N,N,N-trimethyl-4-[(4,7,7-trimethyl-3-oxobicyclo[2,2,1]hept-2-ylidene)methyl]anilinium sulphate; | 52793-97-2 |
| 22 | 3,3,5-Trimethyl cyclohexyl-2-hydroxy benzoate | 118-56-9 |
| 23 | Isopentyl p-methoxycinnamate | 71617-10-2 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate | 6197-30-4 |
| 30 | 2-ethylhexyl 4-(dimethylamino)benzoate | 21245-02-3 |
| 31 | 2-ethylhexyl 4-methoxycinnamate | 5466-77-3 |

TABLE 3-continued

Suitable UV filter substances which can be additionally used
with the UV absorbers according to the present invention

| No. | Chemical Name | CAS No. |
|---|---|---|
| 32 | 2-ethylhexyl salicylate | 118-60-5 |
| 33 | Benzoic acid,4,4',4''-(1,3,5-triazine-2,4,6-triyltriimino]tris-, tris(2-ethylhexyl)ester; 2,4,6-Trianilino-(p-carbo-2'-ethylhexyl-1'-oxi)-1,3,5-triazine | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1-methanesulfonic acid] | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol] | 103597-45-1 |
| 46 | 2,4-bis{[4-(2-ethylhexyloxy)-2-hydroxy]-phenyl}-6-(4-methoxyphenyl)-(1,3,5)-triazine | 187393-00-6 |
| 47 | 1H-Benzimidazole-4,6-disulfonic acid,2,2'-(1,4-phenylene)bis-, disodium salt | 180898-37-7 |
| 48 | Benzoic acid, 4,4'-[[6-[[4-[[(1,1-dimethylethyl)amino]carbonyl]phenyl]amino]1,3,5-triazine-2,4-diyl]diimino]bis-, bis(2-ethylhexyl)ester | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 50 | alpha-(trimethylsilyl)-omega-(trimethyl-silyloxy)poly[oxy(dimethyl)-silylene]-co-[oxy(methyl)(2-{p-[2,2-bis(ethoxycarbonyl)vinyl]phenoxy}-1methyleneethyl)silylene]-co-[oxy(methyl)(2-{p-[2,2-bis(ethoxycarbonyl)vinyl]phenoxy}prop-1-enyl)silylene] | 207574-74-1 |
| 51 | Benzenesulfonic acid, 3-(2H-benzotriazol-2-yl)-4-hydroxy-5-(1-methyl-propyl)-, monosodium salt | 92484-48-5 |
| 52 | Benzoic acid, 2-[4-(diethylamino)-2-hydroxybenzoyl]-, hexyl ester | 302776-68-7 |
| 53 | 1-Dodecanaminium, N-[3-[[4-(dimethylamino)benzoyl]amino]propyl]-N,N-dimethyl-, salt with 4-methylbenzenesulfonic acid (1:1) | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate) | 136-44-7 |
| 62 | Benzeneacetic acid, 3,4-dimethoxy-a-oxo- | 4732-70-1 |
| 63 | 2-Propenoic acid, 2-cyano-3,3-diphenyl-, ethyl ester | 5232-99-5 |

Suitable UV filter substances which can be additionally used with the UV absorber mixture according to the present invention are any UV-A and UV-B filter substances.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$ carboxyl acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants

Diethylhexyl 2,6-naphthalate, di-n-butyl adipate, di(2-ethylhexyl)-adipate, di(2-ethylhexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups.

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alcalin soap of sodium, potassium and ammonium, metallic soap of calcium or magnesium, organic basis soap such as Lauric, palmitic, stearic and oleic acid etc. . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethyl-broide amonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p250-251.

Nonionic bases such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic alkaline bases such as PEG-2 stearate SE, glyceryl stearate SE [Monelgine, Cutina KD], propylene glycol stearate [Tegin P]. Anionic acid bases such as cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic/pharmaceutical preparations, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropylmethylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80 (steareth-10 allyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quarternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/ Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/ butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/ methyl methacrylate-tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5\ H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2, 4-dichlorophenoxy)-phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the UV absorber of formula (1).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Polymeric Beads or Hollow Spheres as SPF Enhancers

The combination of the UV-absorbers and UV-absorber combinations, listed above, with SPF enhancers, such as non-active ingredients like Styrene/acrylates copolymer, silica beads, spheroidal magnesium silicate, crosslinked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased. (EP0893119). Some beads, as mentioned previously, provide a soft feel during spreading. Moreover, the optical activity of such beads, e.g. Micropearl M305, cans modulate skin shine by eliminating reflection phenomena and indirectly may scatter the UV light. When formulated in O/W emulsions, the preferably amount of such SPF enhancers should represent 1% to 10% of the total amount of the emulsion.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol,
in the form of a foam, or
in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

a₁) spontaneously emulsifying stock formulation, consisting of the UV absorber according to the invention, PEG-6-C₁₀oxoalcohol and sorbitan sesquioleate, to which water and any desired quaternary ammonium compound, for example 4% minkamidopropyl dimethyl-2-hydroxyethylammonium chloride or Quaternium 80 is added;

a₂) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions of the UV absorber according to the invention in butyl triglycol and tributyl citrate;

c) mixtures or solutions of the UV absorber according to the invention with n-alkylpyrrolidone.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulgators or emulsifying surfactants, surfactants, dispersing agents, antioxidants, anti-irritants and anti-inflammatory agents etc.

Examples of Cosmetic and Pharmaceutical Preparations (X=Preferred Combinations)

O/W systems:

Ingredients

Emulsifiers

Potassium Cetyl Phosphate 2%-5%
Cetearyl Alcohol/Dicetyl Phosphate/Ceteth-10 Phosphate 2%-6%
Sodium Stearyl Phtalamate 1%-2%
Cetearyl Alcohol/Behentrimonium Methosulfate 1%-5%

| Ingredients | | | | | | | | |
|---|---|---|---|---|---|---|---|---|
| Quaternium-32 1%-5% | | | | X | | | | |
| Dimethicone copolyol/Caprylic/Capric Triglyceride 1%-4% | | | | | X | | | |
| Steareth-2/Steareth-21 2%-5% | | | | | | | X | |
| Polyglyceryl Methyl Glucose Distearate 1%-4% | | | | | | | | X |
| Lipophilic emollient/dispersant oil 15%-20% | X | X | X | X | X | X | X | X |
| Fatty Alcohols and/or Waxes 1%-5% | X | X | X | X | X | X | X | X |
| Thickeners (water swellable thickeners) 0.5%-1.5% | X | X | X | X | X | X | X | X |
| Preservatives 0.5%-1% | X | X | X | X | X | X | X | X |
| Chelating agents (such as EDTA) 0%-0.2% | X | X | X | X | X | X | X | X |
| Antioxidants 0.05%-0.2% | X | X | X | X | X | X | X | X |
| Water deionized Qs 100% | X | X | X | X | X | X | X | X |
| Perfume oils 0.1%-0.4% | X | X | X | X | X | X | X | X |
| UV-absorber according to the invention 1%-20% | X | X | X | X | X | X | X | X |
| UV-absorber as described in table 1-3 0%-30% | X | X | X | X | X | X | X | X |

W/O systems

| Ingredients | 1 | 2 | 3 | 4 | 5 |
|---|---|---|---|---|---|
| Emulsifiers | | | | | |
| Polyglyceryl-2 Dipolyhydroxystearate 2%-4% | X | | | | |
| PEG-30 Dipolyhydroxystearate 2%-4% | | X | | | |
| Rapeseed Oil Sorbitol Esters 1%-5% | | | X | | |
| PEG-45/Dodecyl Glycol Copolymer 1%-5% | | | | X | |
| Sorbitan Oleate/Polycerol-3 ricinoleate 1%-5% | | | | | X |
| Lipophilic emollient/dispersant oil 10%-20% | X | X | X | X | X |
| Fatty Alcohols and/or Waxes 10%-15% | X | X | X | X | X |
| Electrolytes (NaCl, MgSO₄) 0.5%-1% | X | X | X | X | X |
| Polyol phase (Propylene glycol, glycerin) 1%-8% | X | X | X | X | X |
| Preservatives 0.3%-0.8% | X | X | X | X | X |
| Perfume oils 0.1%-0.4% | X | X | X | X | X |
| Chelating agents (such as EDTA) 0%-0.2% | X | X | X | X | X |
| Antioxidants 0.05%-0.2% | X | X | X | X | X |
| Water deionized Qs 100% | X | X | X | X | X |
| UV-absorber according to the invention 1%-20%. | X | X | X | X | X |
| UV-absorber as described in table 1-3 0%-30%. | X | X | X | X | X |

W/Silicone systems

| Ingredients | 1 | 2 | 3 | 4 |
|---|---|---|---|---|
| Emulsifiers | | | | |
| Dimethicone Copolyol/Cyclomethicone 5%-10% | X | | X | |
| Laurylmethicone Copolyol 5%-10% | | X | | X |
| Silicone phase | | | | |
| Cyclopentasiloxane 15%-25% | X | | | X |
| Dimethicone 15%-25% | | X | X | |

| W/Silicone systems | | | | |
|---|---|---|---|---|
| Ingredients | 1 | 2 | 3 | 4 |
| Silicone elastomer | | | | |
| Dimethicone/Vinyldimethicone Crosspolymer 1%-10% | X | X | X | X |
| Humectant/polyols (Propylene glycol, glycerin. . .) 2%-8% | X | X | X | X |
| Chelating agents (such as EDTA) 0%-0.2% | X | X | X | X |
| Antioxidants 0.05%-0.2% | X | X | X | X |
| Preservatives 0.3%-0.8% | X | X | X | X |
| Perfume oils 0.1%-0.4% | X | X | X | X |
| Water deionized Qs 100% | X | X | X | X |
| UV-absorber according to the invention 1%-20% | X | X | X | X |
| UV-absorber as described in table 1-3 0%-30% | X | X | X | X |

| Multiple emulsions | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| Primary emulsion W1/O | | | | | | | | | | | | |
| PEG-30 Dipolyhydroxystearate 2%-6% | X | | | | | | | | | X | | X |
| Cetyl Dimethicone Copolyol 1%-3% | | X | | | | | | X | | | | |
| PEG-30 Dipolyhydroxystearate/Steareth-2/Steareth-21 4%-6% | | | X | | | | X | | | | | |
| Polyglyceryl-2 Dipolyhydroxy-stearate 1%-3% | | | | X | | X | | | | | | |
| Polyglyceryl-6 Ricinoleate 1%-3% | | | | | X | X | | | | X | | |
| Oil phase 15%-30% | | | | | | | | | | | | |
| Fatty acid esters | X | X | X | X | X | | | | | | X | X |
| Natural and synthetic Triglycerides | | | | | | X | X | X | X | X | X | X |
| Hydrocarbon oils | X | X | X | X | X | | | | | | X | X |
| Silicone oils | | | | | | X | X | X | X | X | X | X |
| Preservatives 0.3%-0.8% | X | X | X | X | X | X | X | X | X | X | X | X |
| Water Deioniz. qs 100% | X | X | X | X | X | X | X | X | X | X | X | X |
| Ionic monofunctional O/W emulsifiers | | | | | | | | | | | | |
| Sorbitan Stearate/Sucrose Cocoate 3%-7% | X | | | | | | | X | | | X | |
| Sucrose Laurate 3%-7% | | X | | | | | X | | | X | | |
| Poloxamer 407 3%-7% | | | X | | | X | | X | | | | |
| Polyoxyethylene(20)Sorbate Monoleate 3%-5% | | | | X | X | | | | X | | | |
| Primary emulsion W1/O 50% | X | X | X | X | X | X | X | X | X | X | | |
| Thickeners (water swellable polymers) 0.3%-1% | X | X | X | X | X | X | X | X | X | X | | |
| Water deionized Qs 100% | X | X | X | X | X | X | X | X | X | X | | |
| Perfume oils 0.1%-0.4% | X | X | X | X | X | X | X | X | X | X | | |
| UV-absorber according to the invention 1%-20% | X | X | X | X | X | X | X | X | X | X | | |
| UV-absorber as described in table 1-3 0%-30% | X | X | X | X | X | X | X | X | X | X | | |

| O1/W/O2 emulsions | | | | | | | | |
|---|---|---|---|---|---|---|---|---|
| Ingredients | 1 | 2 | 3 | 4 | 5 | 6 | 7 | 8 |
| Primary emulsion O1/W | | | | | | | | |
| PEG-60 Hydrogenated Castor Oil 25% | X | | | X | X | | | X |
| Steareth-25 25% | | X | X | | | X | X | |
| Oil phase 75% | | | | | | | | |
| Fatty acid esters | X | | X | | | | | |
| Natural and synthetic Triglycerides | | X | | X | | | | |
| Hydrocarbon oils | | | | | X | X | | |
| Silicone oils | | | | | | | X | X |
| Preservatives 0.3%-0.8% | X | X | X | X | X | X | X | X |
| Water deionized Qs 100% | X | X | X | X | X | X | X | X |
| Non ionic multifunctional W/O emulsifier 2%-5% | X | X | X | X | X | X | X | X |
| Waxes 1%-5% | X | X | X | X | X | X | X | X |
| Oil phase 20%-30% | X | X | X | X | X | X | X | X |
| Fatty acid esters | | | | | | | | |
| Natural and synthetic Triglycerides | | | | | | | | |
| Hydrocarbon oils | | | | | | | | |
| Silicone oils | | | | | | | | |
| Primary emulsion O1/W 15% | X | X | X | X | X | X | X | X |
| Electrolytes (NaCl, MgSO$_4$) 0.1%-0.5% | X | X | X | X | X | X | X | X |
| Water deionized Qs 100% | X | X | X | X | X | X | X | X |
| Perfume oils 0.1%-0.4% | X | X | X | X | X | X | X | X |
| uv-absorber according to the invention 1%-20% | X | X | X | X | X | X | X | X |
| uv-absorber as described in table 1-3 0%-30% | X | X | X | X | X | X | X | X |

| Microemulsions | | | | | | | | | | |
|---|---|---|---|---|---|---|---|---|---|---|
| Ingredients | 1 | 2 | 3 | 4 | 5 | 6 | 7 | 8 | 9 | 10 |
| Surfactants | | | | | | | | | | |
| PEG-8 Caprylic/Capric Glycerides 10%-25% | X | | | X | X | | | X | X | |
| PPG-5-ceteth-20 10%-25% | | X | X | | | X | X | | | X |
| Co-surfactants | | | | | | | | | | |
| Polyglyceryl-6 Isostearate 5%-15% | X | | X | | | | | | | |
| Polyglyceryl-3 Diisostearate 5%-15% | | X | | X | | | | | | |
| Polyglyceryl-6 Dioleate 5%-15% | | | | | X | | X | | | |
| PPG-10 Cetyl Ether 5%-15% | | | | | | X | | X | | |
| Ethoxydiglycol 5%-15% | | | | | | | | | X | X |
| Oil phase 10%-80% Isostearyl Benzoate Isostearyl Isostearate PEG-7 Glyceryl Cocoate Cyclomethicone | X | X | X | X | X | X | X | X | X | X |
| Polyalcohols/Humectants 1%-10% | X | X | X | X | X | X | X | X | X | X |
| Preservatives 0.3-0.8% | X | X | X | X | X | X | X | X | X | X |
| Perfume oils 0.1%-0.4% | X | X | X | X | X | X | X | X | X | X |
| Water Deioniz. qs 100% | X | X | X | X | X | X | X | X | X | X |
| uv-absorber according to the invention 1%-20% | X | X | X | X | X | X | X | X | X | X |
| uv-absorber as described in table 1-3 0%-30% | X | X | X | X | X | X | X | X | X | X |

| O/W Spray emulsions | | | | | | |
|---|---|---|---|---|---|---|
| Ingredients | 1 | 2 | 3 | 4 | 5 | 6 |
| Emulsifiers | | | | | | |
| Alkyl Phosphates 0.1%-5% | X | | | X | X | X |
| Glucosidic derivatives 0.1%-5% | | X | X | | | X |
| Solubilisants | | | | | | |
| Ethoxylated Glyceryl ethers 0.1%-1% | X | | X | | | |
| Polysorbates 0.1%-1% | | X | | X | | |
| Ethoxylated Oleyl ethers 0.1%-1% | | | | | X | X |
| Film forming agents | | | | | | |
| PVP/VA Coplymer 1%-10% | X | | X | | X | |
| PVM/MA Copolymer 1%-10% | | X | | X | | X |
| Oil phase 5%-20% Natural oils(Meadowfoam, Jojoba, Macadamia . . .) Fatty acids esters Mineral oils Silicone oils | X | X | X | X | X | X |
| Alcohol 0%-50% | X | X | X | X | X | X |
| Thickeners 0.1%-0.5% Polyacrylates Aluminium/Magnesium Silicates Gums | X | X | X | X | X | X |
| Neutralizing agents 0%-1% | X | X | X | X | X | X |
| Polyalcohols/Humectants 1%-5% | X | X | X | X | X | X |
| Chelating agents (such as EDTA) 0%-0.2% | X | X | X | X | X | X |
| Antioxidants 0.05%-0.2% | X | X | X | X | X | X |
| Water Deioniz. qs 100% | X | X | X | X | X | X |
| Perfume oils 0.1%-0.5% | X | X | X | X | X | X |
| Preservatives 0.4%-1% | X | X | X | X | X | X |
| uv-absorber according to the invention 1%-20% | X | X | X | X | X | X |
| uv-absorber as described in table 1-3 0%-30% | X | X | X | X | X | X |

| G-Aqueous | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| Thickeners | | | | | | | | | | | | |
| Natural Thickener 1%-5% | X | | | | X | X | | | | | | X |
| Semi-symthetic Thickener 1%-5% | | X | | | X | | | X | | | X | |
| Synthetic Thickener 0.3%-1.3% | | | X | X | | | | | X | X | | |
| Neutralizing Agents 0.5%-1.5% | X | X | X | X | X | X | X | X | X | X | X | X |
| Polyols - Humectants 5%-50% | X | X | X | X | X | X | X | X | X | X | X | X |
| Film forming agent/Conditioner | | | | | | | | | | | | |
| Polyquaternium series 1%-5% | X | X | X | | | | X | X | X | | | |
| PVM/MA Copolymer 1%-5% | | | | X | X | X | | | | X | X | X |
| Preservatives 0.5%-1% | X | X | X | X | X | X | X | X | X | X | X | X |
| Chelating Agents (as EDTA) <0.1% | X | X | X | X | X | X | X | X | X | X | X | X |
| Water Deioniz. qs 100% | X | X | X | X | X | X | X | X | X | X | X | X |
| Perfume oils 0.05%-0.4% | X | X | X | X | X | X | X | X | X | X | X | X |
| Solubilisants | | | | | | | | | | | | |
| Ethoxylated Glyceryl ethers 0.1%-5% | X | X | X | | | | | | | | | |
| Polysorbates 0.1%-5% | | | | X | X | X | | | | | | |
| Ethoxylated Oleyl ethers 0.1%-5% | | | | | | | X | X | X | X | X | X |
| uv-absorber according to the invention 1%-20% | X | X | X | X | X | X | X | X | X | X | X | X |
| uv-absorber as described in table 1-3 0%-30% | X | X | X | X | X | X | X | X | X | X | X | X |

| Oleogels | | | | | | | | | | |
|---|---|---|---|---|---|---|---|---|---|---|
| Ingredients | 1 | 2 | 3 | 4 | 5 | 6 | 7 | 8 | 9 | 10 |
| Thickeners | | | | | | | | | | |
| Hydrogenated Lecithin 1%-10% | X | | | | | | | | | X |
| Silica Dimethyl Silylate 1%-10% | | X | | | | | | | X | |
| Silica 1%-5% | | | X | | | | | X | | |
| C$_{24-28}$ Alkyl Dimethicone 1%-5% | | | | X | | | X | | | |
| Aluminium or Magnesium Stearate 1%-5% | | | | | | X | X | | | |
| Polyols - Humectants 5%-70% | X | X | X | X | X | X | X | X | X | X |
| Oil phase 20%-90% | | | | | | | | | | |
| Dicaprylyl Ether | X | | | | | X | | X | | |
| Phenyl Trimethicone | | X | | | | | | X | | |
| Hydrogenated Polyisobutene | | | X | | | | | | | |
| Isopropyl Isostearate | | | | X | | | | | X | |
| Oleogel basis (Mineral oil and hydrogenated Butylene/Ethylene or Ethylene/Propylene Styrene Copolymer) | | | | | X | | | | | X |
| Silicone wax 1%-10% | X | X | X | X | X | X | X | X | X | X |
| Dimethiconol Behenate | | | | | | | | | | |
| Dimethiconol Stearate | | | | | | | | | | |
| Perfume oils 0.1%-0.5% | X | X | X | X | X | X | X | X | X | X |
| Antioxidants 0.05%-0.2% | X | X | X | X | X | X | X | X | X | X |
| UV-absorber according to the invention 1%-20% | X | X | X | X | X | X | X | X | X | X |
| UV-absorber as described in table 1-3 0%-30% | X | X | X | X | X | X | X | X | X | X |

| Light/dry cosmetic oils | | | | |
|---|---|---|---|---|
| Ingredients | 1 | 2 | 3 | 4 |
| Lipophilic base | | | | |
| Hydrocarbon oils 30%-70% | X | | | X |
| Fatty acid esters branched or not 10%-50% | | X | X | |
| Light feel agent | | | | |
| Silicones/Siloxanes 0%-10% | X | | X | |
| Perfluorinated oils and Perfluoroethers 0%-10% | | X | | X |
| Viscosifying agents 0%-10% | X | X | X | X |
| Waxes | | | | |
| Esters of long chain acids and alcohols 0%-2% | X | X | X | X |
| Antioxidants 0.1%-1% | X | X | X | X |
| Solubilisants/dispersing agents 0%-5% | X | X | X | X |
| Perfume oils 0.1%-0.5% | X | X | X | X |
| UV-absorber according to the invention 1%-20%. | X | X | X | X |
| UV-absorber as described in table 1-3 0%-30% | X | X | X | X |

| Foaming/mousse products | |
|---|---|
| Ingredients | |
| SD Alcohol 40 0%-8% | X |
| Propellant 8%-15% | X |
| Nonionic Emulsifier/Surfactant 0.5%-3% | X |
| Corrosion Inhibitor 0%-1% | X |
| Perfume oils 0.1%-0.5% | X |
| Preservatives 0.1%-1% | X |
| Miscellaneous 0%-1% | X |

| Foaming/mousse products | |
|---|---|
| Ingredients | |
| UV-absorber according to the invention 1%-20%. | X |
| UV-absorber as described in table 1-3 0%-30% | X |

| Stick products | |
|---|---|
| Ingredients | |
| Waxes 15%-30% | X |
| Natural and silicone oils 20%-75% | X |
| Lanoline derivatives 5%->50% | X |
| Esters of lanolin | x |
| Acetylated lanolin | x |
| Lanolin oil | x |
| Colorants and pigments 10%-15% | X |
| Antioxidants 0.1%-0.8% | X |
| Perfume oils 0.1%-2% | X |
| Preservatives 0.1%-0.7% | X |
| UV-absorber according to the invention 1%-20% | X |
| UV-absorber as described in table 1-3 0%-30% | X |

| Liquid and compact | | |
|---|---|---|
| Ingredients | 1 | 2 |
| Liquid foundation | | |
| Powder phase 10%-15% | | X |
| Oil phase 30%-40%; 75% (only for anhydrous form) | | X |
| Thickener/suspending agents 1%-5% | | X |
| Film forming polymers 1%-2% | | X |
| Antioxidants 0.1%-1% | | X |
| Perfume oils 0.1%-0.5% | | X |
| Preservatives 0.1%-0.8% | | X |
| Water deionized Qs 100% | | X |

-continued

Liquid and compact

| Ingredients | 1 | 2 |
|---|---|---|
| Compact powder | | |
| Powder phase 15%-50% | | X |
| Oil phase 15%-50% | | X |
| Polyol phase 5%-15% | | X |
| Antioxidants 0.1%-1% | | X |
| Perfume oils 0.1%-0.5% | | X |
| Preservatives 0.1%-0.8% | | X |
| For the two product forms | | |
| UV-absorber according to the invention 1%-20% | X | X |
| UV-absorber as described in table 1-3 0%-30% | X | X |

Conditioning Shampoos

| Ingredients | 1 |
|---|---|
| Primary surfactants (listed previously) 5%-10% | X |
| Secondary surfactants (listed previously) 5%-15% | X |
| Foam Stabilizers (listed previously) 0%-5% | X |
| Water deionized 40%-70% | X |
| Actives 0-10% | X |
| Conditioners | x |
| Refatting agents | x |
| Moisturizing agents | x |
| Thickeners/Rheology mofifiers 0%-3% | X |
| Humectants 0%-2% | X |
| PH adjusting agents 0%-1% | X |
| Preservatives 0.05%-1% | X |
| Perfume oils 0.1%-1% | X |
| Antioxidants 0.05%-0.20% | X |
| Chelating Agents (EDTA) 0%-0.2% | X |
| Opascifying agents 0%-2% | X |
| UV-absorber according to the invention 1%-20% | X |
| UV-absorber as described in table 1-3 0%-30% | X |

The cosmetic preparation according to the invention is distinguished by excellent protection of human skin against the damaging effect of sunlight.

The following Examples serve to illustrate the invention but do not limit the invention thereto. The cosmetic active substances are primarily given with their INCI name (INCI=International Norm of Cosmetical Ingredients).

EXAMPLE 1

Preparation of Micronised Methylene Bis-Benzotriazolyl Tetramethylbutylphenol 50 parts of methylene bis-benzotriazolyl tetramethylbutylphenol and 50 parts of octyl triazone are ground together with a grinding medium of zirconium silicate sand, a protective surfactant (alkyl polyglucoside) and water in a bead mill to form a mixed micropigment having a $d_{50}$ of 190 nm. When the grinding medium has been separated off, the suspension of the mixed micropigment can be used in the preparation of sunscreen formulations.

EXAMPLE 2

Preparation of Micronised Titanium Dioxide

A method to manufacture an oil dispersion comprises milling in the presence of a particulate grinding medium particulate titanium dioxide in an oil and in the presence of an organic dispersing agent for said $TiO_2$ in said oil, in which the amount of said $TiO_2$ is such that the dispersion has a solids content of greater than 40% by weight and continuing said milling for a period of time such that the particulate $TiO_2$ has an average size of from 10 nm to 150 nm. This method is described in GB-A-2206339A.

The oil can be vegetable oils, fatty acid glycerides, fatty acid esters or fatty alcohols. Typically, the dispersing agent can be polyesters or salts of hydroxycarboxylic acid or free carboxylic acid, monoesters of fatty acid alkanolamides and carboxylic acids and their salts, or alternative dispersing agents as polymers or copolymers of acrylic or methacrylic acids, e.g. block copolymers of such monomers. The quantity of the dispersing agent used can be an amount of from 5% to 35%, preferably 5% to 20% by weight based on the weight of $TiO_2$.

Another method to generate a dust-free and stabile solid micronised UV filter having an average primary particle size smaller than 150 nm is described in U.S. Pat. No. 5,811,082.

10 to 80 parts by weight of $TiO_2$ pigment are dispersed in 90 to 20 parts by weight of wax; natural wax, for example vegetable waxes (Carnauba, Candelilla, Jojoba), animal waxes (beeswax, lanolin wax), mineral waxes (paraffin, ceresin, ozocerite) or synthetic waxes (polyethylene waxes, propylene waxes, long chain fatty alcohols waxes, long chain carboxylic acids waxes) or waxy surfactants (anionic, cationic, non ionic).

EXAMPLE 3

Oil/Water Sun Care Cream with High SPF

| | INCI-Name | % w/w (as supplied) |
|---|---|---|
| Part A | cetyl alcohol | 1.0 |
| | $C_{12-15}$ alkyl benzoate | 2.0 |
| | cetearyl isononanoate | 2.0 |
| | stearyl dimethicone | 1.0 |
| | ethoxydiglycol | 2.0 |
| | dimethicone copolyol/ caprylic capric triglyceride | 3.0 |
| | dioctyl Ether | 2.0 |
| | isohexadecane | 1.0 |
| | titanium dioxide micropigment from Example 2 | 10.00 |
| Part B | steareth-10 allyl ether/ acrylates copolymers | 0.80 |
| | disodium EDTA | 0.2 |
| | Aqua | qs to 100 |
| | sodium acrylates copolymer and paraffinium liquidum and PPG-1 Trideceth-6 | 1.50 |
| Part C | phenyl trimethicone | 0.75 |
| | Cyclopentasiloxane (and) Dimethicone/Vinyl Dimethicone Crosspolymer | 0.5 |
| Part D | methylene bis-benzotriazolyl tetramethylbutylphenol micropigment from example 2 | 15.00 |
| | aqua | 20.00 |
| Part E | Phenoxyethanol(and)Methylparaben(and) Ethylparaben(and) Butylparaben(and)Propylparaben(and) Isobutylparaben | 0.8 |

PH value: 6.31 RT = 24.9° C.
aspect: white bright cream
SPF: 19.4

Operating Mode:

Part A is heated until 75° C. and under gentle stirring.

Part B is prepared, without incorporating the sodium acrylates copolymer, and heated until 80° C. under moderate stirring. Then part A is added into the part B under high stirring and then, the remaining sodium acrylates copolymer is added immediately. Part C is premixed at room temperature the until a homogeneous liquid is obtained, then poored into the emulsion at around 65-60° C. and homogenized with Turrax during a short time (5 sec. at 10 000 rpm).

Premix, at room temperature, the part D until you get a homogeneous liquid, then poor it into the emulsion at around 60-50° C. Let cool down the emulsion under gentle stirring until 30-35° C., and then add the part E. Finally, adjust pH around 6.5-7.0 with NaOH 30% dispersion.

EXAMPLE 4

Oil/Water Sun Care Cream High SPF

|  | INCI-Name | % w/w (as supplied) |
|---|---|---|
| Part A | cetyl alcohol | 1.0 |
|  | $C_{12-15}$ alkyl benzoate | 2.0 |
|  | cetearyl isononanoate | 2.0 |
|  | stearyl dimethicone | 1.0 |
|  | ethoxydiglycol | 2.0 |
|  | Dimethicone Copolyol/Caprylic Capric triglyceride | 3.0 |
|  | Dioctyl Ether | 2.0 |
|  | Isohexadecane | 1.0 |
|  | Ethylhexyl Methoxycinnamate | 3.0 |
|  | titanium dioxide micropigment from Example 2 | 10.00 |
| Part B | steareth-10 allyl ether/ acrylates copolymers | 0.80 |
|  | disodium EDTA | 0.2 |
|  | Aqua | qs to 100 |
|  | Sodium Acrylates copolymer and paraffinium liquidum and PPG-1 trideceth-6 | 1.50 |
| Part C | Phenyl Trimethicone | 0.75 |
|  | Cyclopentasiloxane (and) Dimethicone/Vinyl Dimethicone Crosspolymer | 0.5 |
| Part D | methylene bis-benzotriazolyl tetramethylbutylphenol micropigment from example 2 | 15.00 |
|  | Aqua | 20.00 |
| Part E | Phenoxyethanol(and)Methylparaben(and) Ethylparaben(and)Butylparaben(and)Propylparaben(and) Isobutylparaben | 0.8 | pH value: 6.28
RT = 24.9° C.
Aspect: white bright cream
SPF: 67.5

Operating Mode:

Part A is heated until 75° C. and under gentle stirring.

Part B is prepared without incorporating the sodium acrylates copolymer, and heated until 80° C. under moderate stirring. Then part A is add into part B under high stirring and then, the remaining sodium acrylates copolymer is added immediately. Part C is premixed at room temperature until a homogeneous liquid is obtained, then poored into the emulsion at around 65-60° C. and then homogenized with Turrax during a short time (5 sec. at 10 000 rpm).

Part D is premixed at room temperature until a homogeneous liquid is obtained, which is then poored into the emulsion at around 60-50° C. The emulsion is cooled down under gentle stirring until 30-35° C., and then part E is added.

Finally, pH is adjusted with NaOH 30% dispersion around 6.5-7.0.

The invention claimed is:

1. UV-absorber mixture, comprising
(a) 1% to 60% by weight of a micronised UV broadband absorber of formula

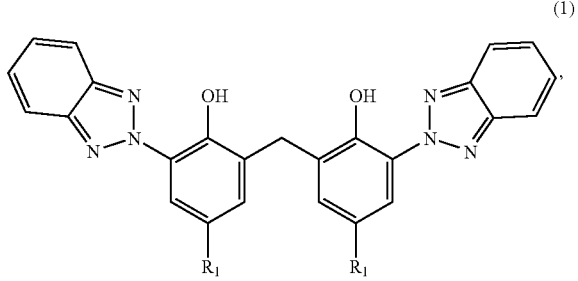

(1)

wherein $R_1$ is $C_1$-$C_{12}$alkyl; or phenyl-substituted $C_1$-$C_{12}$alkyl; and
(b) 1% to 60% by weight of a water dispersible and/or oil-dispersible coated titanium dioxide wherein said titanium dioxide is pre-coated with a material selected from the group consisting of silica, iron dioxide, alumina and zinc to impart a hydrophilic surface.

2. Mixture according to claim 1, wherein $R_1$ is iso-octyl.

3. Mixture according to claim 1, wherein component (b) is oil-dispersible titanium dioxide coated with metal soaps to impart a hydrophobic surface.

4. Mixture according to claim 3, wherein the metal soap is aluminium stearate, magnesium stearate, aluminium laurate or zinc stearate.

5. Mixture according to claim 1, which comprises a further UV absorber.

6. Mixture according to claim 5, wherein the further UV absorber is selected from cinnamic acid amides, which correspond to formula

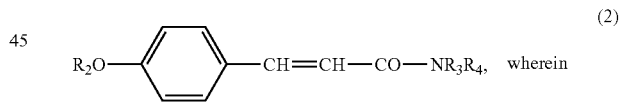

(2)

$R_2O$—⟨phenyl⟩—CH=CH—CO—$NR_3R_4$, wherein $R_2$ is hydrogen or $C_1$-$C_5$alkoxy,
$R_3$ is hydrogen or $C_1$-$C_5$alkyl, and
$R_4$ is —(CONH)$_m$-phenyl,
m is 0 or 1; and the phenyl group is unsubstituted or substituted by one, two or three of the radicals OH, $C_1$-$C_3$alkyl, $C_1$-$C_3$alkoxy and CO—$OR_5$.
$R_5$ is hydrogen; an alkali metal; an ammonium group —$N(R_6)_4$;
$R_6$ is hydrogen, $C_1$-$C_5$alkyl; or a polyoxyethylene radical that has from 1 to 10 ethylene oxide units and the terminal OH group can be etherified with a $C_1$-$C_5$alcohol.

7. Mixture according to claim 6, wherein the cinnamic acid derivative is 2-ethylhexyl-4-methoxy-cinnamate.

8. A cosmetic formulation, comprising a UV-absorber mixture according to claim 1, and also cosmetically acceptable carriers or adjuvants.

* * * * *

UNITED STATES PATENT AND TRADEMARK OFFICE
CERTIFICATE OF CORRECTION

PATENT NO. : 7,357,918 B2 Page 1 of 1
APPLICATION NO. : 10/503151
DATED : April 15, 2008
INVENTOR(S) : Christine Comte et al.

It is certified that error appears in the above-identified patent and that said Letters Patent is hereby corrected as shown below:

On title page

Item (86) should read:

-- (86)   PCT No.:     PCT/EP03/00649 --.

Signed and Sealed this

Fifth Day of August, 2008

JON W. DUDAS
*Director of the United States Patent and Trademark Office*